United States Patent [19]

Shinohara et al.

[11] Patent Number: 5,136,073

[45] Date of Patent: Aug. 4, 1992

[54] THEXYL TRIALKOXY SILANE

[75] Inventors: Toshio Shinohara, Takasaki; Muneo Kudo; Motoaki Iwabuchi, both of Annaka, all of Japan

[73] Assignee: Shin-Etsu Chemical Co., Ltd., Tokyo, Japan

[21] Appl. No.: 796,360

[22] Filed: Nov. 22, 1991

[30] Foreign Application Priority Data

Nov. 29, 1990 [JP] Japan .................. 2-331760

[51] Int. Cl.$^5$ .............................................. C07F 7/18
[52] U.S. Cl. .................................................. 556/482
[58] Field of Search ........................................ 556/482

[56] References Cited

U.S. PATENT DOCUMENTS

| | | | |
|---|---|---|---|
| 2,985,678 | 5/1961 | Chappelow et al. | 556/482 X |
| 3,291,742 | 12/1966 | Millward | 556/482 X |
| 3,576,030 | 4/1971 | Alsgaard | 556/482 X |
| 3,839,383 | 10/1974 | Kotzsch et al. | 556/482 X |
| 4,695,643 | 9/1987 | Oertle et al. | 556/482 X |

*Primary Examiner*—Paul F. Shaver
*Attorney, Agent, or Firm*—Henry T. Burke

[57] ABSTRACT

Several thexyl trialkoxy silanes as a novel class of organosilicon compounds were synthesized by the reaction of dehydrochlorination condensation between thexyl trichlorosilane and an alcohol, e.g., methyl, ethyl, isopropyl and isobutyl alcohols, and characterized by the analytical data. These compounds are useful as an intermediate in the synthetic preparation of other organosilicon compounds, starting material of various silicones, surface-treatment agent of inorganic materials and additive in complex catalysts.

6 Claims, 4 Drawing Sheets

THEXYL TRIALKOXY SILANE

BACKGROUND OF THE INVENTION

The present invention relates to a novel organosilicon compound. More particularly, the invention relates to a novel organosilane compound having a thexyl group bonded to the silicon atom not known in the prior art nor described in any literatures.

SUMMARY OF THE INVENTION

Thus, the novel organosilicon compound provided by the invention is a thexyl trialkoxy silane represented by the general formula $$H-CMe_2-CMe_2-Si(OR)_3 \quad (I)$$

in which Me is a methyl group and R is an alkyl group.

DETAILED DESCRIPTION OF THE PREFERRED EMBODIMENTS

Figure 1:
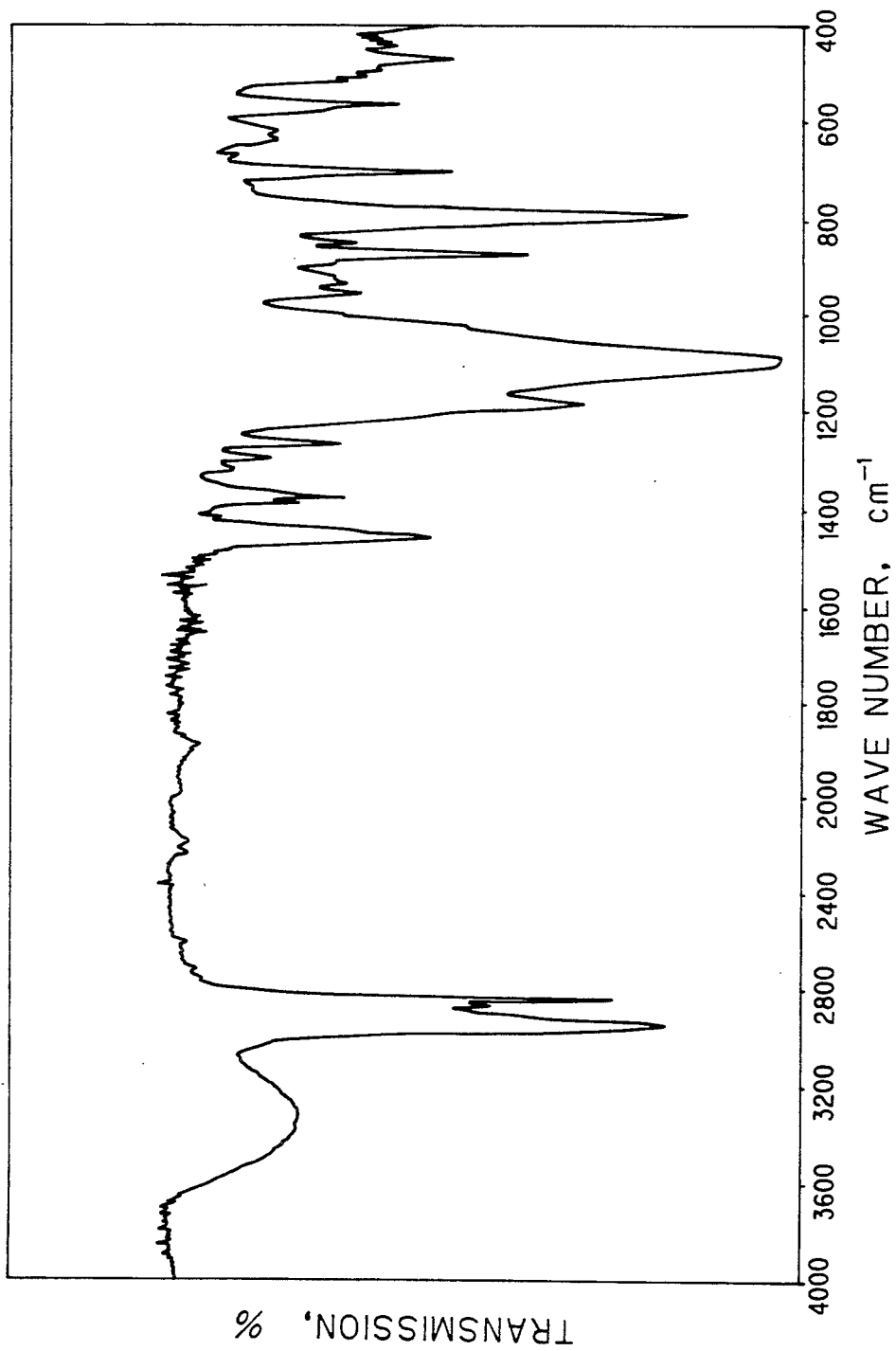
FIGS. 1, 2, 3 and 4 are each an infrared absorption spectrum of thexyl trimethoxy silane, thexyl triethoxy silane, thexyl triisopropoxy silane and thexyl triisobutoxy silane, respectively, prepared in the examples.

Several organosilicon compounds having a thexyl group, i.e. 1,1,2-trimethylpropyl group, bonded to the silicon atom are known including thexyl trichlorosilane reported in Journal of American Chemical Society, volume 70, page 484 (1948) and Chem. Listy, volume 52, page 640 (1958) and thexyl dimethyl chlorosilane reported in Tetrahedron Letters, volume 26, page 5511 and page 5515 (1985).

By virtue of the relatively bulky thexyl group bonded to the silicon atom of the silane compound, these thexyl silane compounds are expected to be a useful compound in the industry of organosilicon compounds or so-called silicones, for example, as an intermediate in the preparation of silicone resins, dispersion aid of a finely divided silica filler used in the preparation of silicone rubber compositions and a surface-treatment agent of various kinds of inorganic materials as well as an additive in the preparation of complex catalysts.

The above mentioned chlorosilanes having a thexyl group in a molecule, however, are not quite advantageous for use in actual applications because the silicon-bonded chlorine atoms readily produce very corrosive hydrogen chloride when the compound is reacted with a compound or substrate having an active hydrogen atom in the molecule such as water. Namely, hydrogen chloride is a very notorious pollutant of the environment so that use of a thexyl-containing chlorosilane is greatly limited as a strating material of silicones, surface-treatment agent of inorganic materials, additive in complex catalysts and the like.

In view of the above described situations, the inventors have continued extensive investigations to obtain a thexyl-containing organosilane compound free from the above described problems and disadvantages arriving at a discovery that a thexyl trialkoxy silane can well meet the purpose to establish the present invention after conducting detailed studies on the method for obtaining such a compound.

Thus, the thexyl trialkoxy silane, i.e. 1,1,2-trimethylpropyl trialkoxy silane, is a compound represented by the general formula $$H-CMe_2-CMe_2-Si(OR)_3, \quad (I)$$

in which Me is a methyl group and R is an alkyl group. The alkyl group denoted by R has, for example, 1 to 8 carbon atoms and is exemplified by methyl, ethyl, n-propyl, isopropyl, n-buyl, isobutyl, tert-butyl, n-pentyl, isopentyl, n-hexyl and n-octyl groups.

Such a thexyl trialkoxy silane can be prepared by the reaction of thexyl trichlorosilane, which is a known compound, expressed by the structural formula $$H-CMe_2-CMe_2-SiCl_3,$$

in which Me is a methyl group, and an alcohol represented by the general formula $$ROH,$$

in which R has the same meaning as defined above, by heating a mixture thereof undiluted or diluted with a suitable organic solvent such as hydrocarbon solvents, ether solvents and the like in the presence of a hydrogen chloride acceptor at a temperature in the range from 20° to 150° C. or, preferably, from 30° to 100° C. for 0.5 to 30 hours under agitation. It is a convenient way to conduct the reaction under reflux of the alcohol used as the reactant in the reaction mixture.

In conducting the above described reaction, the amount of the alcohol should be in the range from 3 to 4 moles per mole of thexyl trichlorosilane. When the reaction mixture is diluted with an organic solvent, the solvent should be a hydrocarbon solvent, e.g., benzene, toluene, xylene, n hexane, cyclohexane, methyl cyclohexane and the like, or an ether solvent, e.g., diethyl ether, dibutyl ether, tetrahydrofuran, dioxane and the like, although it is a possible way that the alcohol as one of the reactants is used in an excessive amount so as to serve also as a solvent. The hydrogen chloride acceptor can be any of known ones including tertiary amines such as triethyl amine, tripropyl amine, tributyl amine and DBU, i.e. 1,5-diazabicyclo[5.4.0]undec-5-ene, and urea. The use of urea as a hydrogen chloride acceptor is sometimes advantageous because hydrochloride of urea is formed in the reaction mixture in a separate liquid phase so that it can be readily separated by the technique of liquid-phase separation without undertaking the rather laborious procedure of filtration. The amount of the hydrogen chloride acceptor is from 3 to 4 moles per mole of thexyl trichlorosilane.

In the following, examples are given to illustrate the procedure of synthetic preparation and characterization of several thexyl trialkoxy silanes.

EXAMPLE 1

Into a four-necked flask of 200 ml capacity equipped with a stirrer, reflux condenser, dropping funnel and thermometer were introduced 10.6 g (0.33 mole) of methyl alcohol and 19.8 g (0.33 mole) of urea to form a mixture, into which 20.0 g (0.091 mole) of thexyl trichlorosilane were added dropwise through the dropping funnel taking 30 minutes under agitation of the reaction mixture. Since no particular cooling means was undertaken, the temperature of the reaction mixture was varied from 20° to 50° C. during the dropwise addition of the silane. After completion of the dropwise addition of thexyl trichlorosilane, the temperature of the reaction mixture in the flask was increased to 70 to 80° C. and agitation was continued for additional 6 hours at this temperature to complete the reaction. Thereafter, the reaction mixture was kept standing so that phase separation took place into layers, of which the lower layer was discarded. The liquid in the upper layer was taken and subjected to distillation under reduced pressure to give 13.3 g of a fraction boiling at 84° C. under a pressure of 27 mmHg. This product could be identified to be thexyl trimethoxy silane from the analytical results shown below so that the above mentioned yield of the product corresponded to 0.065 mole or 71% of the theoretical yield.

Mass spectrum: m/z: 206 (M+); 121 (M+-Me$_2$CH-CMe$_2$)

Nuclear magnetic resonance spectrum: $^1$H-NMR (CCL$_4$, 60 MHz), δ (ppm) 3.60 (s, 9H); 1.8–1.3 (m, 1H); 0.95 (s, 6H); 0.93 (d, 6H, J=6Hz)

Infrared absorption spectrum: See FIG. 1.

EXAMPLE 2

The synthetic procedure was substantially the same as in Example 1 excepting replacement of the methyl alcohol with the same molar amount, i.e. 15.2 g (0.33 mole), of ethyl alcohol. Distillation of the upper layer obtained by the phase separation of the reaction mixture gave 20.1 g of a fraction boiling at 67° C. under a pressure of 3 mmHg. This product could be identified to be thexyl triethoxy silane from the analytical results shown below so that the above mentioned yield of the product corresponded to 0.081 mole or 89% of the theoretical yield.

Mass spectrum: m/z: 248 (M+); 203 (M+-EtO); 163 (M+-Me$_2$CHCMe$_2$)

Nuclear magnetic resonance spectrum: $^1$H-NMR (CCl$_4$, 60 MHz), δ (ppm) 3.81 (q, 6H, J=7Hz); 1.8–1.4 (m, 1H); 1.18 (t, 9H, J=7Hz); 0.88 (s, 6H); 0.86 (d, 6H, J=6Hz)

Figure 2:
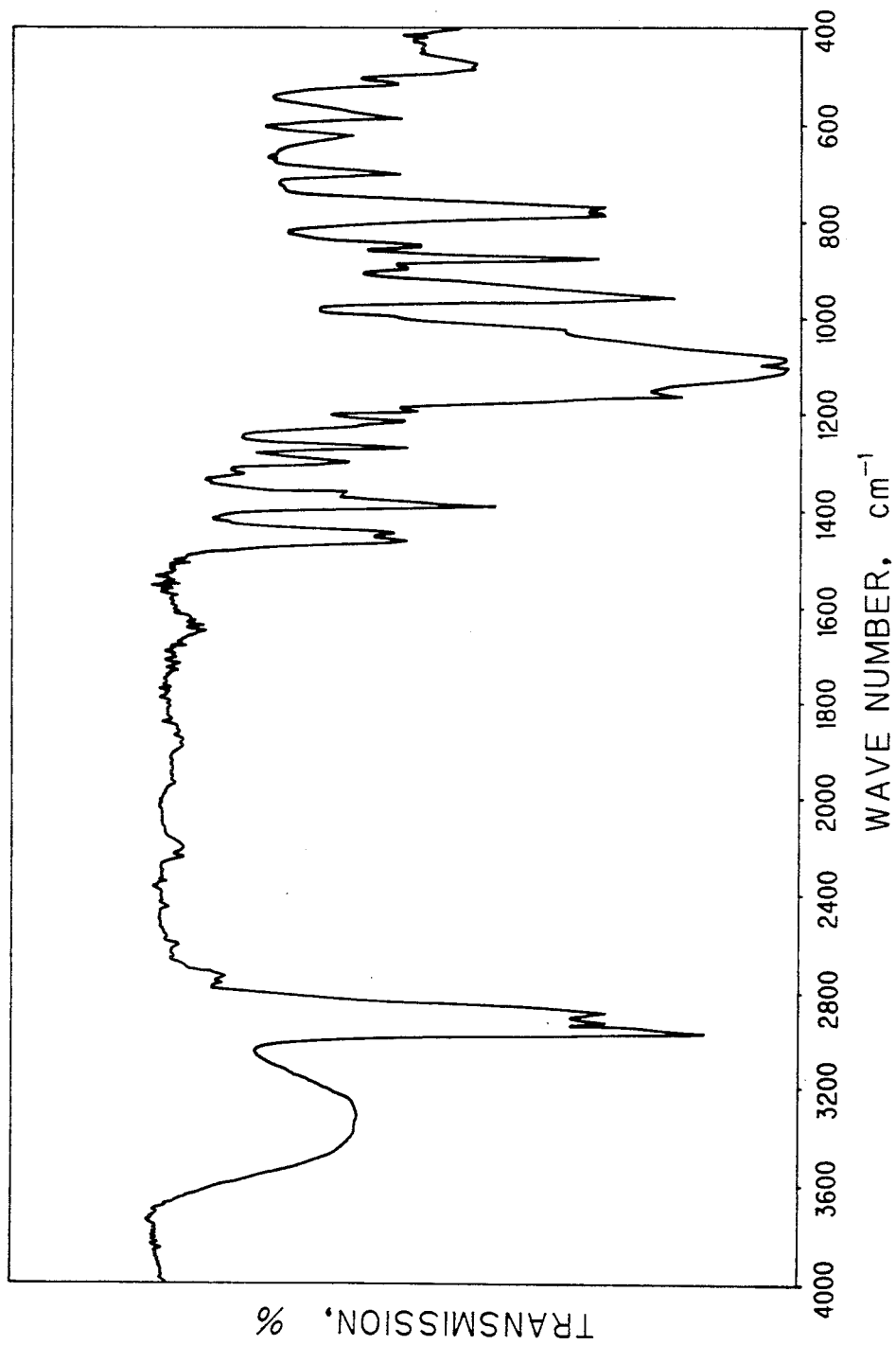

Infrared absorption spectrum: See FIG. 2.

EXAMPLE 3

The synthetic procedure was substantially the same as in Example 1 excepting replacement of the methyl alcohol with the same molar amount, i.e. 19.8 g (0.33 mole), of isopropyl alcohol. Distillation of the upper layer obtained by the phase separation of the reaction mixture gave 22.9 g of a fraction boiling at 73° C. under a pressure of 3 mmHg. This product could be identified to be thexyl triisopropoxy silane from the analytical results shown below so that the above mentioned yield of the product corresponded to 0.079 mole or 87% of the theoretical yield.

Mass spectrum: m/z: 275 (M+-Me); 231 (M+-PrO); 205 (M+-Me$_2$CHCMe$_2$)

Nuclear magnetic resonance spectrum: $^1$H-NMR (CCl$_4$, 60 MHz), δ (ppm) 4.21 (h, 3H, J=6Hz); 1.9–1.4 (m, 1H); 1.19 (d, 18H, J=6Hz); 0.90 (d, 6H, J=56Hz)

Figure 3:
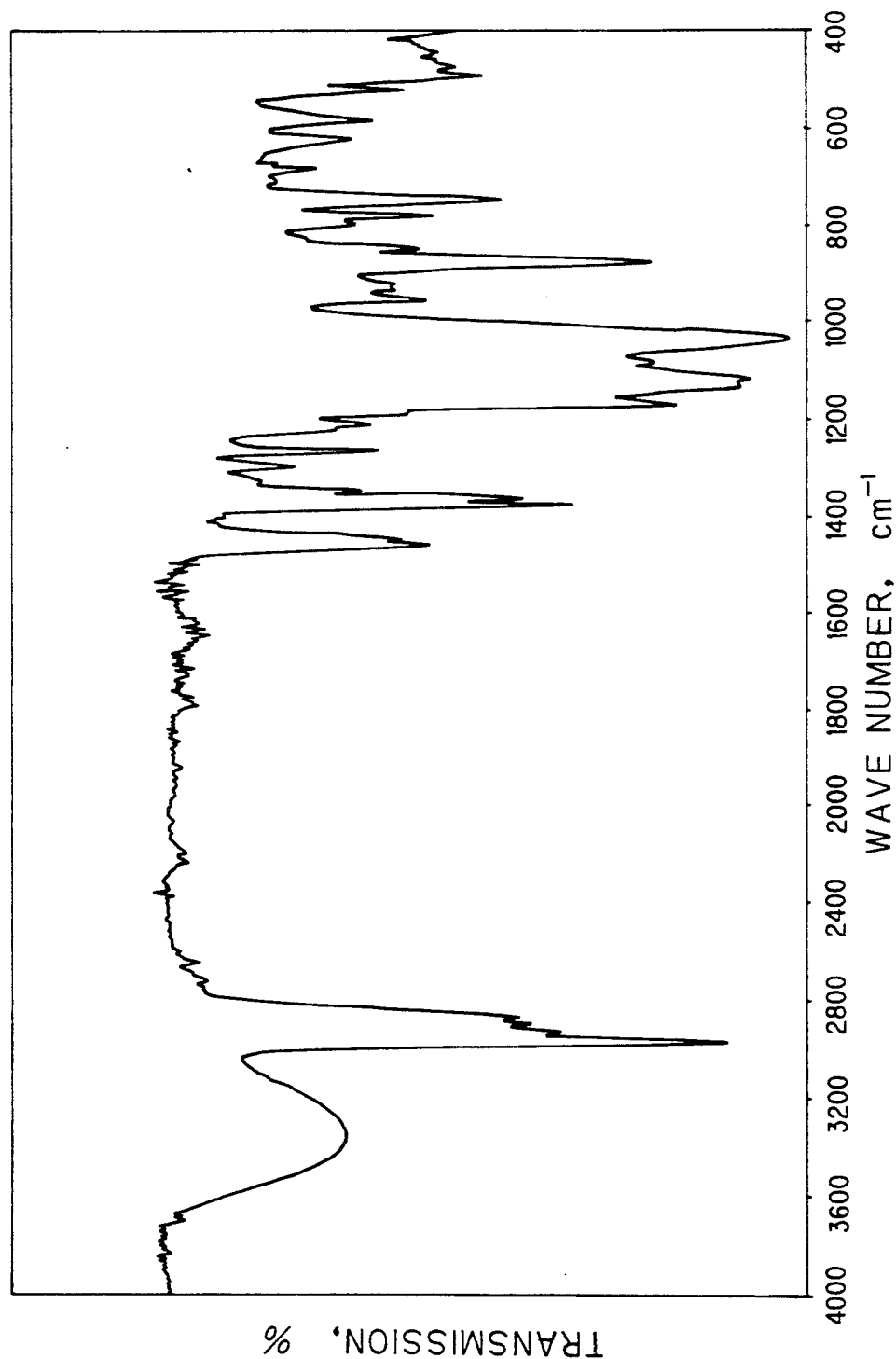

Infrared absorption spectrum: See FIG. 3.

EXAMPLE 4

The synthetic procedure was substantially the same as in Example 1 excepting replacement of the methyl alcohol with the same molar amount, i.e. 24.4 q (0.33 mole), of isobutyl alcohol. Distillation of the upper layer obtained by the phase separation of the reaction mixture gave 22.9 g of a fraction boiling at 102°–103° C. under a pressure of 3 mmUg. This product could be identified to be thexyl triisobutoxy silane from the analytical results shown below so that the above mentioned yield of the product corresponded to 0.069 mole or 76% of the theoretical yield.

Mass spectrum: m/z: 259 (M+-BuO); 247 (M+-Me$_2$CHCMe$_2$)

Nuclear magnetic resonance spectrum: $^1$H-NMR (CCl$_4$, 60 MHz), δ (ppm) 3.62 (d, 6H, J=6Hz); 2.1–1.4 (m, 4H); 1.01 (d, 24H, J=6Hz); 1.00 (s, 6H)

Figure 4:
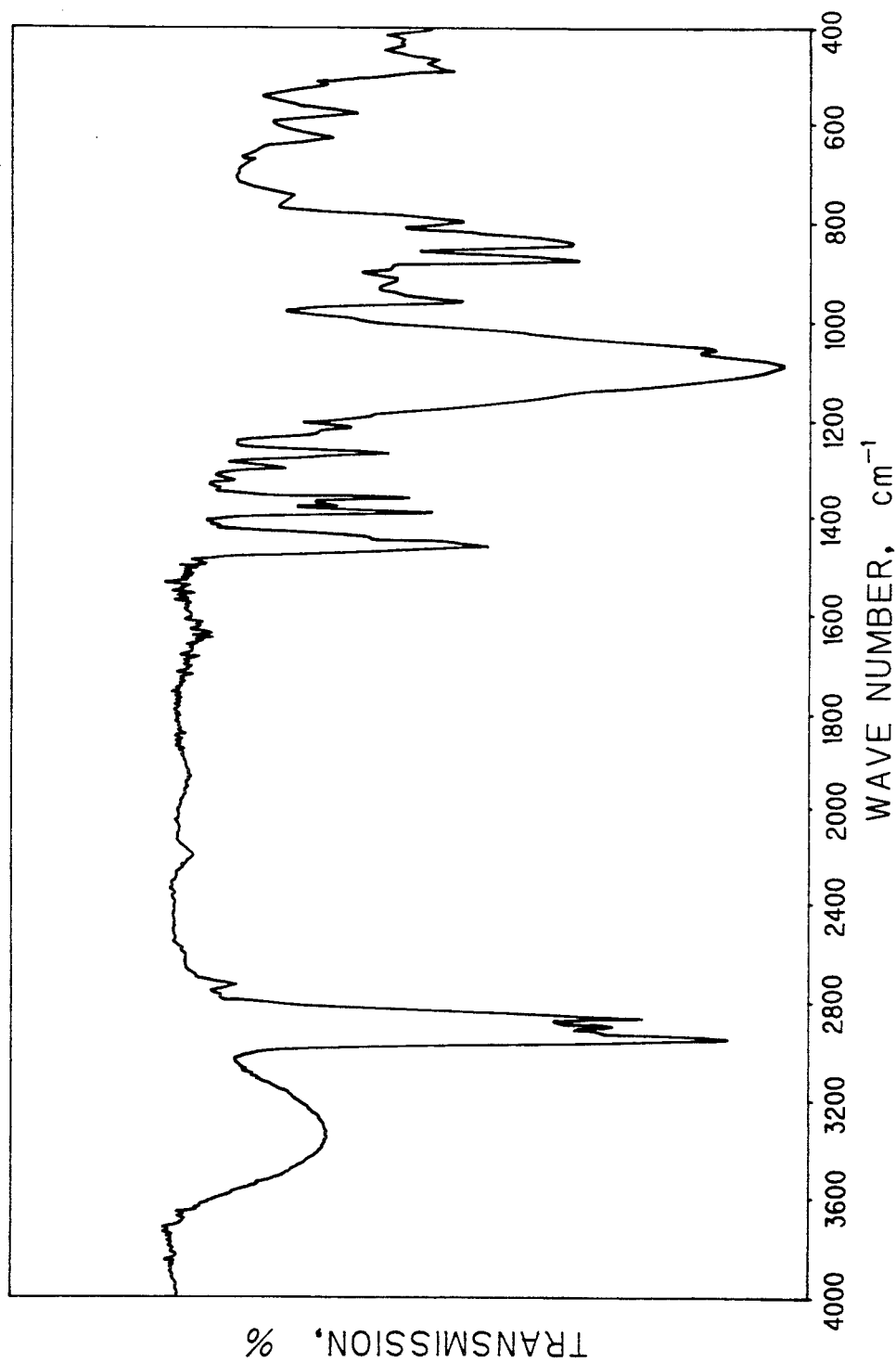

Infrared absorption spectrum See FIG. 4.

What is claimed is:

1. A thexyl trialkoxy silane represented by the general formula

$H-CMe_2-CMe_2-Si(OR)_3$, in which Me is a methyl group and R is an alkyl group.

2. The thexyl trialkoxy silane as claimed in claim 1 in which the alkyl group denoted by R has 1 to 8 carbon atoms.

3. The thexyl trialkoxy silane as claimed in claim 2 in which the group denoted by R is a methyl group.

4. The thexyl trialkoxy silane as claimed in claim 2 in which the group denoted by R is an ethyl group.

5. The thexyl trialkoxy silane as claimed in claim 2 in which the group denoted by R is an isopropyl group.

6. The thexyl trialkoxy silane as claimed in claim 2 in which the group denoted by R is an isobutyl group.

* * * * *